(12) United States Patent
Noel et al.

(10) Patent No.: US 11,116,809 B2
(45) Date of Patent: Sep. 14, 2021

(54) BIOPOLYMER COMPOSITIONS FOR THE TREATMENT AND PREVENTION OF LIVER DISEASE

(71) Applicant: ProMend Animal Health, Inc., Germantown, TN (US)

(72) Inventors: Scott P. Noel, Germantown, TN (US); John Kirk Shumpert, Germantown, TN (US); Alex Greene, Germantown, TN (US); William Brian Austin, Germantown, TN (US)

( * ) Notice: Subject to any disclaimer, the term of this patent is extended or adjusted under 35 U.S.C. 154(b) by 328 days.

(21) Appl. No.: 16/023,267

(22) Filed: Jun. 29, 2018

(65) Prior Publication Data
US 2019/0000903 A1   Jan. 3, 2019

Related U.S. Application Data

(60) Provisional application No. 62/527,822, filed on Jun. 30, 2017.

(51) Int. Cl.
| | |
|---|---|
| *A61K 36/28* | (2006.01) |
| *A61K 36/288* | (2006.01) |
| *A61K 31/198* | (2006.01) |
| *A61P 1/04* | (2006.01) |
| *A61K 36/074* | (2006.01) |
| *A61P 1/16* | (2006.01) |
| *A61K 36/21* | (2006.01) |
| *A61K 47/26* | (2006.01) |
| *A61K 47/46* | (2006.01) |
| *A61K 47/24* | (2006.01) |
| *A61K 47/14* | (2017.01) |
| *A61K 36/886* | (2006.01) |
| *A61K 9/00* | (2006.01) |
| *A61K 47/36* | (2006.01) |
| *A23L 5/00* | (2016.01) |
| *A61K 47/12* | (2006.01) |
| *A61K 47/10* | (2017.01) |
| *A61K 47/22* | (2006.01) |

(52) U.S. Cl.
CPC ............ *A61K 36/28* (2013.01); *A23L 5/00* (2016.08); *A61K 9/0056* (2013.01); *A61K 31/198* (2013.01); *A61K 36/074* (2013.01); *A61K 36/21* (2013.01); *A61K 36/288* (2013.01); *A61K 36/886* (2013.01); *A61K 47/10* (2013.01); *A61K 47/12* (2013.01); *A61K 47/14* (2013.01); *A61K 47/22* (2013.01); *A61K 47/24* (2013.01); *A61K 47/26* (2013.01); *A61K 47/36* (2013.01); *A61K 47/46* (2013.01); *A61P 1/04* (2018.01); *A61P 1/16* (2018.01)

(58) Field of Classification Search
None
See application file for complete search history.

(56) References Cited

U.S. PATENT DOCUMENTS

| | | | | |
|---|---|---|---|---|
| 2008/0305096 | A1* | 12/2008 | Verdegem | A61K 9/205 424/94.4 |
| 2010/0021533 | A1* | 1/2010 | Mazed | A61K 36/54 424/450 |
| 2010/0074969 | A1* | 3/2010 | Hughes | A61K 36/886 424/655 |
| 2010/0233320 | A1* | 9/2010 | Sunvold | A23K 40/25 426/62 |
| 2012/0164252 | A1* | 6/2012 | Kano | A23L 33/105 424/765 |
| 2019/0381110 | A1* | 12/2019 | Noel | A61K 35/644 |
| 2020/0129564 | A1 | 4/2020 | Noel et al. | |
| 2020/0149084 | A1* | 5/2020 | Frettloh | A23L 33/15 |

FOREIGN PATENT DOCUMENTS

WO    WO 99/61038    * 12/1999

* cited by examiner

*Primary Examiner* — Ralph J Gitomer

(74) *Attorney, Agent, or Firm* — Greenberg Traurig, LLP; Melissa Hunter-Ensor; Nicholas Ballor

(57) ABSTRACT

The invention provides compositions comprising milk thistle, dandelion root, and/or one or more antioxidant amino acids (e.g., n-acetyl L-cysteine) for the treatment and prevention of liver disease (hepatic insufficiency) in a mammal (e.g., equine). The composition may further comprise chitosan and/or additional components that prevent or treat liver disease or hepatic insufficiency (e.g., inulin, prebiotics).

17 Claims, No Drawings

BIOPOLYMER COMPOSITIONS FOR THE TREATMENT AND PREVENTION OF LIVER DISEASE

CROSS-REFERENCE TO RELATED APPLICATIONS

This application claims priority to and benefit of U.S. Provisional Application No. 62/527,822, filed Jun. 30, 2017, the entire contents of which are incorporated herein by reference.

BACKGROUND OF THE INVENTION

The liver is an organ found in all vertebrates that is responsible for many important functions including detoxification and filtering of blood and other biochemicals, protein synthesis, production of digestive chemicals, and metabolizes drugs. The liver also plays an important role, along with other organs, to digest, process, and metabolize foods.

Liver Disease, also known as hepatic insufficiency, develops when the liver organ is no longer able to perform the functions of the liver in an optimal manner. Symptoms of liver distress related to liver disease or hepatic insufficiency often include weakness, fatigue, nausea, vomiting, weight loss, and jaundice. Without treatment, liver disease may lead to permanent injury to the liver. Once the liver has been permanently impaired, short term options such as dialysis are possible, but no long term solutions currently exist to support the lost liver functions. As liver cells die or are injured, indicative of liver disease, enzymes are released that can be detected as diagnostic measures of liver disease.

The equine liver functions similarly to all vertebrate liver organs, functioning for the production and secretion of bile, blood filtrations, metabolic processes, protein syntheses, detoxification, and hormone production. The equine liver can be considered as three zones, with Zone 1, innermost (closest) to portal circulation, being most metabolically active with the most exposure to oxygen, nutrients, and toxins. Zone 3, furthest from portal circulation, is the least metabolically active and is important to enzyme activity. Zone 3 is most susceptible to damage from decreased oxygen levels resulting from liver disease, as this zone is the last one oxygenated.

Equine Liver Disease is relatively rare and presents clinically only after at least 70% of the organ is affected. Equine liver impairment is generally associated with filtering and detoxification functionality of the organ, specifically with respect to portal circulation. Clinical symptoms of liver disease in horses include weight loss, loss of appetite, colic, skin sensitivity to sunlight, yellowing of the skin, or mucous membranes (jaundice). Liver failure may include developing blindness, ataxia (lack of coordination), edema, stomach impaction, or laryngeal paralysis.

Causes of equine liver disease can be acute or chronic, and may be related to viruses, obstruction of bile ducts, administration of serum products, or diet. One of the most common causes of liver disease in equine is bile duct obstruction, which can lead to inflammation of the liver cells (cholangiohepatitis). Obstructions and inflammation can lead to bile stones that present as fever, abdominal pain, photosensitivity, and weight loss. This is typically treated with antibiotics, drugs to break up the obstruction, and possibly surgical removal. Another cause, administration of serum products causing serum associated hepatitis (Theiler's Disease) can occur rapidly due to the liver being unable to remove toxins from the blood. Disease duration is on the order of hours to days. Typical treatments include intravenous fluids, glucose, pH balancing, antibiotics, and nutraceuticals, with the intent of keeping the equine alive during the course of the disease. Finally, diet plays an important role in liver disease. Several plant species are toxic to horses and may be inadvertently incorporated into equine feed. Some of these plants are highly toxic, containing pyrrolizidine alkaloids (PA) resulting in high mortality rates after exposure. Several drug and nutraceutical options are used to attempt to mitigate plant toxin damage. Ultimately, diagnosis of liver disease causation is often difficult, but when possible, removing the animal from causative factors quickly can play an important role in recovery.

In the absence of other causative factors, horses in training often present with elevated liver enzyme levels associated with liver disease. These symptoms suggest some level of liver damage, but do not necessarily present as an impairment to liver function. While the mechanisms remain unknown, young thoroughbred horses in race training often respond to decreased training and rest.

Current treatments include supporting therapies such as nutritional supplements and decreased activity or rest. While some liver disease markers such as gamma-glutamyl transferase (GGT) enzyme levels may take time to decrease, the liver will generally heal itself quickly once the disease-causing factor has been discontinued. Supportive therapies are intended to treat the liver disease factors while allowing horses in training to continue without the need for behavioral modifications. Accordingly, improved compositions and methods for treating equine liver disease are urgently required.

Equine liver function can be measured through several methods. Enzymatic testing is important to indicate the presence of a disease, but do not necessarily correlate to measurement of liver function. Enzymatic tests such as the presence of GGT or alkaline phosphatase (ALP) indicate problems associated with the biliary tract (bile duct obstruction, etc.), while levels of glutamate dehydrogenase (GLDH), sorbitol dehydrogenase (SDH), and aspartate aminotransferase (AST) are used to track injuries to liver cells (hepatocellular injury). Furthermore, bilirubin concentrations can be used to test for biliary obstruction. Bile acids can be tested to indicate the presence of chronic disease, and globulin and iron levels can be tested to further indicate the response to inflammation and liver function, respectively. GGT enzymatic testing is often the first line of testing and the most common in evaluation of liver issues. GGT levels may take weeks to decrease even after the causative stimulus has been removed, but decreasing GGT levels are generally associated with the insult to the liver no longer being present and healing taking place. Following enzymatic testing, a biopsy may be necessary to further evaluate liver damage and function.

SUMMARY OF THE INVENTION

The invention provides compositions comprising milk thistle, dandelion root, and/or one or more antioxidant amino acids (e.g., n-acetyl L-cysteine) or precursors thereof. The composition may further comprise chitosan, and/or one or more additional components that promotes digestive health (e.g., inulin, probiotics) for the treatment and prevention of gastric ulcers (e.g., esophageal, stomach, or duodenum) in a mammal (e.g., equine), including humans.

In one embodiment, the invention features a composition for the treatment or prevention of liver disease containing any of the ingredients in Table 1 and a biopolymer that is any one or more of chitosan, cellulose, collagen, and alginate in a form suitable for oral administration. In one embodiment, the composition further contains slippery elm. In another embodiment, the composition further contains inulin or another probiotic. In another embodiment, the composition further contains aloe water and/or aloe vera. In another embodiment, the composition further contains one or more acids selected from the group consisting of ascorbic acid, citric acid, malic acid, apple cider vinegar, rice vinegar or other acetic acids or vinegars. In another embodiment, the composition further contains lecithin. In another embodiment, the composition further contains a flavoring selected from the group consisting of apple, apple butter, apple pectin, peppermint, and citrus. In another embodiment, the composition further contains a plant-based composition selected from the group consisting of a pomace, powder, liquid, concentrate, and a lyophilized component. In another embodiment, the composition further contains a fungal composition (e.g., derived from a mushroom, such as schizophyllan) or a plant-based composition derived from a fruit (e.g., banana, berry, apple, or citrus fruit, such as orange, lemon, lime), vegetable (e.g., beet, beetroot, other root-based flora), grain or herb. In one embodiment, the plant-based composition has anti-inflammatory activity. In another embodiment, the composition further contains a preservative that is ascorbic acid, potassium sorbate or citric acid. In another embodiment, the composition further contains a polyol selected from the group consisting of glycerol, glycerine, glycerin, maltitol, sorbitol, xylitol, erythritol, or isomalt. In another embodiment, the composition further contains an omega-3 fatty acid and/or hyaluronic acid. In another embodiment, the chitosan is present in the range of 0.00001 to 10 wt %, from 0.00001 to 5 wt %, or from 0.00001 to 3 wt %. In another embodiment, the manuka honey is present in the range of 0.00001 to 10 wt %, from 0.00001 to 5 wt %, or from 0.00001 to 3 wt %. In another embodiment, the lecithin is present in the range of 0.00001 to 25 wt %, preferably from 0.00001 to 10 wt %. In another embodiment, acids are present individually in the range of 0.00001 to 10 wt %, from 0.00001 to 5 wt %, from 0.00001 to 3 wt %, and collectively not more than 5% of the composition. In another embodiment, the composition is a liquid, gel, semi-liquid, semi-solid, paste, or solid form. In another embodiment, water makes up the balance of the solution, and represents no less than 60 wt % of the entire solution. In another embodiment, the composition is formulated for delivery through a syringe, formed into a powder, feed, feed additive, or treat. In another embodiment, the composition further contains a soluble or insoluble nano-particulate. In another embodiment, the nano-particulate is Silver, Magnesium, Copper, Arsenic, Zinc, Tellurium, or Mercury. In another embodiment, the composition contains a soluble or insoluble antimicrobial, antifungal, or antibacterial agents.

In another aspect, the invention features a pharmaceutical composition containing the composition of a previous aspect.

In another aspect, the invention features a method for treating liver disease in a subject, the method involving administering to the subject an effective amount of a composition of any previous aspect.

In another aspect, the invention features a method for treating or preventing a liver disease, the method involving administering to the subject an effective amount of a composition of any previous aspect. In one embodiment, the subject has hepatic insufficiency, hepatocellular injury, or hepatic dysfunction.

In another aspect, the invention features a method for maintaining a healthy liver (hepatic) organ in a subject, the method involving administering to the subject an effective amount of a composition of any previous aspect.

In various embodiments of the above aspects, the subject is a mammal. In various embodiments, the mammal is a non-human primate, a human, an equine, bovine, ovine, feline, or canine.

Definitions

By "alginate" is meant the sodium salt of alginic acid. In particular embodiments, alginic acid refers to a linear copolymer with homopolymeric blocks of (1-4)-linked 1-D-mannuronate (M) and its C-5 epimer .alpha.-L-guluronate (G) residues, respectively, covalently linked together in different sequences or blocks.

By "chitosan" is meant a chitin-derived polymer that is at least 20% deacetylated. Preferably, chitosan is at least about 50% deacetylated. Chitin is a linear polysaccharide consisting of (1-4)-linked 2-acetamido-2-deoxy-b-D-glucopyranose. Chitosan is a linear polysaccharide consisting of (1-4)-linked 2-amino-2-deoxy-b-D-glucopyranose.

By "acid treated chitosan" is meant chitosan that is solubilized in an acidic solution.

By "collagen" is meant a protein component of an extracellular matrix having a tertiary structure that includes polypeptide chains intertwining to form a collagen triple helix or having a characteristic amino acid composition comprising Gly-X-Y repeat units, or a fragment thereof. Collagens useful in the methods of the invention include any collagen known in the art (e.g., one of collagen type 1-29).

By "composite" is meant a mixture of materials.

By "agent" is meant any small compound, macromolecule, biopolymer, polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels.

By "antimicrobial" is meant an agent that inhibits or stabilizes the proliferation or survival of a microbe. In one embodiment, a bacteriostatic agent is an antimicrobial. In other embodiments, any agent that kills a microbe (e.g., bacterium, fungus, virus) is an antimicrobial.

By "anti-inflammatory" is meant an agent that reduces the severity or symptoms of an inflammatory reaction in a tissue.

By "clinician" is meant any healthcare provider. Exemplary clinicians include, but are not limited to, doctors, veterinarians, osteopaths, physician's assistants, emergency medical technicians, medics, nurse practitioners, and nurses.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages or interferes with the normal function of a cell, tissue, or organ. In one example, a disease is an ulcer or other wound affecting the gastrointestinal system of a mammal.

By "effective amount" is meant the amount of an agent required to ameliorate the symptoms of a disease relative to an untreated patient. The effective amount of active agent(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "polymer" is meant a natural or synthetic organic molecule formed by combining smaller molecules in a regular pattern.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

By "subject" is meant a mammal, including, but not limited to, a human or non-human mammal, such as a non-human primate, a bovine, equine, canine, ovine, or feline.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "reference" is meant a standard or control condition.

DETAILED DESCRIPTION OF THE INVENTION

The invention provides compositions comprising milk thistle, dandelion root, and/or one or more antioxidant amino acids (e.g., n-acetyl L-cysteine) or precursors thereof. The composition may further comprise chitosan, manuka honey, and/or one or more additional components that promotes digestive health and/or liver health (e.g., inulin, probiotics).

The composition may be used for the treatment and/or prevention of gastric ulcers (e.g., esophageal, stomach, or duodenum) and/or liver disease (hepatic insufficiency, hepatic injury, or hepatocellular injury) in a mammalian subject. In an embodiment, the subject is equine. In an embodiment, the subject is a human. The present invention approaches liver treatment from a wound care perspective, whether protecting and preventing ulcers or treating existing ulcers.

A nutraceutical composition of the invention may be used temporarily (e.g., for a few days, weeks) or may be used on an on-going basis (e.g., months, years) as a permanent daily use supplement, or may be used to treat an acute condition following the onset or suspicion that liver disease symptoms are present.

Equine Liver Health

The liver is an organ found in all vertebrates that is responsible for many important functions including detoxification and filtering of blood and other biochemicals, protein synthesis, production of digestive chemicals, and metabolizes drugs. The liver also plays an important role, along with other organs, to digest, process, and metabolize foods.

Liver Disease, also known as hepatic insufficiency, develops when the liver organ is no longer able to perform the functions of the liver in an optimal manner. Symptoms of liver distress related to liver disease or hepatic insufficiency often includes weakness, fatigue, nausea, vomiting, weight loss, and jaundice. Without treatment, liver disease may lead to permanent injury to the liver. Once the liver has been permanently impaired, short term options such as dialysis are possible, but no long term solutions currently exist to support the lost liver functions. As liver cells die or are injured, indicative of liver disease, enzymes are released that can be detected as diagnostic measures of liver disease.

The equine liver functions similarly to all vertebrate liver organs, functioning for the production and secretion of bile, blood filtrations, metabolic processes, protein syntheses, detoxification, and hormone production. The equine liver can be considered as three zones, with Zone 1, innermost (closest) to portal circulation, being most metabolically active with the most exposure to oxygen, nutrients, and toxins. Zone 3, furthest from portal circulation, is the least metabolically active and is important to enzyme activity. Zone 3 is most susceptible to damage from decreased oxygen levels resulting from liver disease, as this zone is the last oxygenated.

Equine Liver Disease is relatively rare and presents clinically only after at least 70% of the organ is affected. Equine liver impairment is generally associated with filtering and detoxification functionality of the organ, specifically with respect to portal circulation. Clinical symptoms of liver disease in horses include weight loss, loss of appetite, colic, skin sensitivity to sunlight, yellowing of the skin or mucous membranes (jaundice). Liver failure may include developing blindness, ataxia (uncoordinated), edema, stomach impaction, or laryngeal paralysis.

Causes of Equine Liver Disease can be acute or chronic, and may be related to viruses, obstruction of bile ducts, administration of serum products, or diet. One of the most common causes of liver disease in equine is bile duct obstruction, which can lead to inflammation of the liver cells (cholangiohepatitis). These obstructions and inflammation can lead to bile stones that present as fever, abdominal pain, photosensitivity, and weight loss. This is typically treated with antibiotics, drugs to break up the obstruction, and possibly surgical removal. Another cause, administration of serum products causing serum associated hepatitis (Theiler's Disease) can occur rapidly due to the liver being unable to remove toxins from the blood. Disease duration is on the order of hours to days. Typical treatments include intravenous fluids, glucose, pH balancing, antibiotics, and nutraceuticals, with the intent of keeping the equine alive during the course of the disease. Finally, diet plays an important role in liver disease. Several plant species are toxic to horses and may be inadvertently incorporated into equine feed. Some of these plants are highly toxic, containing pyrrolizidine alkaloids (PA) resulting in high mortality rates when exposed. Several drug and nutraceutical options are used to attempt to mitigate plant toxin damage. Ultimately, diagnosis of liver disease causation is often difficult, but when possible, removing from causative factors quickly can play an important role in recovery.

In the absence of other causative factors, horses in training often present with elevated liver enzyme levels associated with liver disease. These symptoms suggest some level of liver damage, but do not necessarily present as an impairment to liver function. While the mechanisms remain unknown, young thoroughbred horses in race training often respond to decreased training and rest.

Current treatments include supporting therapies such as nutritional supplements and decreased activity or rest. While some liver disease markers such as GGT enzyme levels may take time to decrease, the liver will generally heal itself quickly once the disease-causing factor has been discontinued. Supportive therapies are intended to treat the liver disease factors while allowing horses in training to continue without the need for behavioral modifications. Accordingly, improved compositions and methods for treating equine liver disease are urgently required.

Equine liver function can be measured through several methods. Enzymatic testing is important to indicate the presence of a disease, but do not necessarily correlate to measurement of liver function. Enzymatic tests such as the presence of gamma glutamyl transferase (GGT) or alkaline phosphatase (ALP) indicate problems associated with the biliary tract (bile duct obstruction, etc.), while levels of glutamate dehydrogenase (GLDH), sorbitol dehydrogenase (SDH), and aspartate aminotransferase (AST) are used to track injuries to liver cells (hepatocellular injury). Furthermore, Bilirubin concentrations can be used to test for biliary obstruction. Bile acids can be tested to indicate the presence of chronic disease, and globulin and iron levels can be tested to further indicate the response to inflammation and liver function, respectively. GGT enzymatic testing is often the first line of testing and the most common in evaluation of liver issues. GGT levels may take weeks to decrease even after the causative stimulus has been removed, but decreasing GGT levels are generally associated with the insult to the liver no longer being present and healing taking place. Following enzymatic testing, biopsy may be necessary to further evaluate liver damage and function.

Nonlimiting examples of animals affected by liver disease and treatable by the methods and formulations of the invention particularly include young (foals) and adult equine animals (horses). Other animals that may suffer from liver disease and benefit from treatment and prevention by the methods and compositions described herein include canines, felines, young camels (calves) and adult camels. In addition, young cattle (calves), pigs (piglets), sheep (lambs), goats (kids), and adult animals, including, cattle, steer, bison, buffalo, goats, sheep and rams, may be treated according to the methods of the invention.

In some embodiments, a composition of the invention is used to treat a human subject.

Chitosan

Chitosan is a naturally occurring linear polysaccharide composed of randomly distributed β-(1-4)-2-amino-2-D-glucosamine (deacetylated) and β-(1-4)-2-acetamido-2-D-glucoseamine (acetylated) units. Chitosan is derived from chitin, a naturally occurring polymer. Chitin is a white, hard, inelastic, nitrogenous polysaccharide isolated from fungi, mollusks, or from the exoskeletons of arthropods (e.g., crustaceans, insects). The major procedure for obtaining chitosan is the alkaline deacetylation of chitin with strong alkaline solution. Generally, the raw material is crushed, washed with water or detergent, and ground into small pieces. After grinding, the raw material is treated with alkali and acid to isolate the polymer from the raw crushed material. The polymer is then deacetylated by treatment with alkali. Chitin and chitosan differ in their degrees of deacetylation (DDA). Chitin has a degree of deacetylation of 0% while pure chitosan has a degree of deacetylation of 100%. Typically, when the degree of deacetylation is greater than about 50% the polymer is referred to as chitosan.

Chitosan is a cationic weak base that is substantially insoluble in water and organic solvents. Typically, chitosan is fairly soluble in dilute acid solutions, such as acetic, citric, oxalic, propionic, ascorbic, hydrochloric, formic, and lactic acids, as well as other organic and inorganic acids. Chitosan's charge gives it bioadhesive properties that allow it to bind to negatively charged surfaces, such as biological tissues present in a gastrointestinal tract of an animal.

In the body chitosan is degraded by lysozyme, N-acetyl-o-glucosaminidase and lipases. Lysozyme degrades chitosan by cleaving the glycosidic bonds between the repeating chitosan units. The byproducts of chitosan degradation are saccharides and glucosamines that are gradually absorbed by the body.

This biopolymer material has been used medically, and is valued for its biocompatibility, degradation and absorption properties, hemostatic properties, and for promoting the healing process in damaged tissues. Chitosan has also been linked in scientific literature as being antimicrobial, bacteriostatic, anti-inflammatory, and for reducing itching. Chitosan has been used as coating, a composition binder, and as an active ingredient in pharmaceutical and nutraceutical applications.

Collagen

Collagen is the most abundant structural protein in the body, existing as the foremost component of the extracellular matrix (ECM). Most types of collagen contain a unique tertiary structure that includes three individual right-handed helical polypeptide chains intertwining to form a left-handed helix. Collagen has a characteristic amino acid composition comprised of Gly-X-Y repeat units. Collagen is used in a variety of medical applications including hemostatic materials, biocompatible coatings, drug delivery and tissue engineering. Collagen-based biomaterials are also used in soft-tissue engineering and repair. In the past two decades, a multitude of medical products composed of collagen have been approved by the FDA, and many are available as commercial products, including collagen-based corneal shields, anti-infectious catheters, tissue sealants, hemostatic sponges, and topical wound dressing products. Collagen is also used as a tissue engineering substrate for skin, bone, and blood vessel replacement.

Healing Agents

The invention provides pharmaceutical and/or nutraceutical compositions comprising a biopolymer (e.g., chitin, chitosan, collagen, cellulose, alginate, dextrose) and one or more herbal supplements, prebiotics, probiotics, acids, fruits, vegetables, plants (flora), preservatives, polyols, medicaments, antimicrobial additives, antibacterial additives, antifungal additives, or nano-particles. The current embodiment may be provided as a liquid or solid, in the form of powder, hydrogel, paste, pellets, or larger solid compositions.

The invention provides a chitosan solution with varying viscosity comprising natural healing agents, such as manuka honey. Manuka honey is a highly viscous type of honey that has medical applications, as well as antimicrobial and flavoring properties.

In particular embodiments, a chitosan composition described herein comprises an herbal supplements, including but not limited to milk thistle and dandelion root. Milk thistle contains silymarin as its main active ingredient. Silymarin has both anti-inflammatory and antioxidant properties. Milk thistle has been used for many years as a natural remedy for liver disease as well as other medical conditions. Dandelion root is similar in that it is a natural remedy for many medical conditions and has been used in this manner for many years. Specifically, dandelion has been used to treat liver issues as well as infection-related conditions.

In particular embodiments, a chitosan composition described herein comprises a prebiotic. Prebiotics useful in a composition of the invention, including but not limited to inulin may be added to a composition of the invention to support digestive health. Inulin is a prebiotic fiber that not only supports digestive health, vitamin absorption and supports healthy motility.

In particular embodiments, a chitosan composition described herein comprises one or more acids including, but not limited to, acetic or citric acid, which may be used as a solvent, preservative, flavoring, etc. Acids may be used, for example, as a solvent to dissolve a biopolymer of the invention. In one embodiment a polymer that is present in powder form is dissolved in a liquid solution with varying viscosity. This may be performed by pouring a known mass of biopolymer component together with an acid solvent solution; and mixing until the powder biopolymer is fully dissolved into a liquid solution. Other agents may be added to solution. Depending on viscosity, it may be necessary to apply negative pressure (a vacuum) to the resulting solution prior to filling the container of choice (bottle, tube, syringe, etc.). Further, acids may be used as a preservative to prevent spoilage of the resulting solution, and to maintain or increase shelf life. Acids, such as citric or malic acid, may also be used to affect the flavor profile of the resulting solution as well.

In particular embodiments, a chitosan composition described herein comprises lecithin. Lecithin is the common name for a fat called phosphatidylcholine. Lecithin has been shown to reduce stress and anxiety in horses in training, a known cause of increased liver enzymes.

In particular embodiments, a chitosan composition described herein comprises one or more natural and/or synthetic flavorings to create a palatable nutraceutical. Animals, in particular, are unlikely to show willingness to consume a nutraceutical unless it is flavored in a manner that is appealing. Common flavorings favored by equines include, but are not limited to apple, peppermint, or citrus flavors.

In particular embodiments, a chitosan composition described herein comprises one or more fruits, vegetables, herbs, or other plant-based compositions. Advantageously, such fruits, vegetables, and herbs have antioxidant or anti-inflammatory properties. In one particular embodiment, a chitosan composition comprises a plant-based pomace. Pomace is the pulpy residue that remains after the plant materials have been pressed or crushed to extract its juice. Fruits, vegetables, herbs, and plants may be provided in the form of pomace, such as a powder, liquid, solid or concentrated form based on the whole or a part of the flora. Common examples of pomace include, but are not limited to, apple powder, beet powder, beetroot powder, banana or banana peel powder, and compositions from berries (for example, blueberry, blackberry, raspberry, strawberry, cranberry).

In particular embodiments, a chitosan composition described herein comprises a polyol, including but not limited to glycerol, glycerine, or glycerin, malitol, sorbitol, xylitol, erithritol, or isomalt, which are a group of sugar alcohols that may be used to provide sweetening while maintaining moisture content in the resulting solution. In one embodiment, one or more polyols are added to a composition of the invention to maintain the moisture of the composition, binding the nutraceutical composition in paste form for optimum ingredient activity, while additionally affecting the flavor profile.

The resulting solution, which may vary in viscosity, may in another embodiment have a nano-particulate dispersed within the solution. Nano-particulate silver and nano-particulate magnesium may be used to prevent bacterial, microbial, or fungal contamination of the solution itself or in the treated local environment. Further nano-particulate metals and non-metals have been shown to interact at the cellular level, which may have a preservative, or active pharmaceutical or medicinal effect. Bioactive ingredients, such as bioactive metals (e.g., Copper, Arsenic, Zinc, Tellurium, Mercury) in varying size ranges may also be added.

Anti-Inflammatory Agents

The compositions described herein may further comprise an anti-inflammatory agent, e.g., omega fatty acids, such as omega-3 fatty acids and/or hyaluronic acid.

In a typical diet, there is consumption of omega fatty acids. Omega fatty acids are called essential fatty acids because the body cannot produce them; therefore, they must be consumed through dietary intake. Omega-3 fatty acids are anti-inflammatory, while omega-6 fatty acid consumption can lead to increased pro-inflammatory chemical secretion within the body. Increased omega-6 to omega-3 ratios in dietary intake have led to increases non-alcoholic fatty liver disease, among other compromising liver conditions. Typical ratios of omega-6 to omega-3 fatty acid consumption fall between 12:1 to 25:1 (inclusive), or between 4:1 to 1:1 (inclusive). Omega-3 fatty acid supplementation can aid in reducing the pro-inflammatory effects of high levels of omega-6 and other inflammation-causing agents associated with certain conditions or activities that elicit inflammation in the body, such as disease, training, stress, etc.

Hyaluronic acid (HA), in particular, high molecular weight HA, is another anti-inflammatory agent. The addition of HA to a supplement would offset the negative actions of an increased inflammation of the liver (or other organs). Hyaluronic acid is routinely consumed orally in supplements and the effects of HA on inflammation are well-understood by the skilled practitioner in the art.

Other natural sources of anti-inflammatory agents include, but are not limited to, green leafy vegetables, bok choy, broccoli, blueberries, pineapples, celery, beets, walnuts, salmon and other fishes, ginger, etc. Herbs that are anti-inflammatory include, but are not limited to, turmeric, cayenne, cinnamon, cloves, sage, rosemary, etc. Other anti-inflammatory agents include alpha-lipoic acid, curcumin, resveratrol, spirulina, etc.

Other agents that can aid in reducing the damaging effects of liver stress are glutathione, acetyl-L-carnitine, methionine, SAM-e (S-adenosylmethionine) and primrose oil. These agents can be used to detoxify, modify chemical balances, and/or supplement the body's natural production of the chemicals in an effort to promote liver health.

Any or all of the above-described anti-inflammatory agents (ingredients) can be added to a supplement, composition, or formulation as described and exemplified herein to reduce the overall inflammation caused by inflammation-inducing conditions or activities, for example, stress, training, diet, disease, or other causative actions or conditions. Any or all of these agents (ingredients) can be added to the compositions and formulations described and exemplified herein in doses determined by a practitioner in the art using conventional methods, in an effort to offset conditions that cause increased inflammation in the liver and/or the body. These agents (ingredients) can be added in any of the dosable forms described herein, including paste, chew, powder, solution, liquid, etc. The ingredients in the formulation can be added together and lyophilized to form a powder that is consumed, without limitation, in capsule form, or added to a liquid drink or to a consumable food. In an embodiment, a liquid based supplement containing an anti-inflammatory agent, for example, could be capsuled in a manner similar to omega-3 fish oil supplements.

In one embodiment, the invention provides a composition comprising chitosan and herbal supplements in any proportion (e.g., 0.5:10, 1:10, 2:20, 3:10, 4:10, 5:10, 6:10, 7:10, 8:10, 9:10, 10:0.5, 10:1, 10:2, 10:3, 10:4, 10:5, 10:6, 10:7, 10:8, 10:9, 1:1), further characterized by the addition of one or more of the following:

Reishi mushroom,
Beet root,
N-acetyl L-cysteine,
Artichoke,
Inulin as a prebiotic,
Ascorbic, citric, and malic acids,
Lecithin,
Apple Pectin,
Apple (powder)
Potassium Sorbate (as a preservative)
Propylparaben, methylparaben (as a preservative)
Aloe Vera
Glycerin In another embodiment, the composition further comprises an anti-inflammatory agent. In a particular embodiment, the anti-inflammatory agent is an omega fatty acid, e.g., omega-3 fatty acid, hyaluronic acid, or both an omega fatty acid and hyaluronic acid.

Pharmaceutical and Nutraceutical Formulations

In one embodiment, a composition of the invention for use in treating or preventing liver disease is a paste or a gel composition. Admixed and/or otherwise associated or combined with the gel or paste phase is one or more healing agents formulated for oral administration. By way of example, a composition of the invention is formulated for oral or buccal administration, including, without limitation, roof of mouth, dental, periodontal, or esophageal administration. In particular embodiments, food source (animal feed), nutrition source, libation source, or food and/or drink supplement could be used. In an embodiment, the combination product could be provided in an aqueous formulation, administered to the animal as a drench or directly from a ready-to-use (RTU) bottle directed to the esophageal cavity. In a related embodiment, administration can also be by inclusion in the regular or special diet of the animal, such as in a functional food for the animals in need, or as a dietary supplement or food supplement for administration to an animal in need thereof according to the present invention.

Nonlimiting examples of suitable carriers, excipients, diluents and vehicles include lactose, dextrose, sucrose, sorbitol, mannitol, starches, gum acacia, calcium phosphate, alginates, calcium silicate, microcrystalline cellulose, polyvinylpyrrolidone, cellulose, collagen, gelatin, syrup, methyl cellulose, methyl- and propylhydroxybenzoates, talc, magnesium, stearate, water, mineral oil, edible oils, and the like. The formulations can also include lubricating agents, wetting agents, emulsifying and suspending agents, preserving agents, sweetening agents or flavoring agents.

Formulations of the invention include ranges of the following ingredients in Table 1.

TABLE 1

| Ingredient | Percentage |
| --- | --- |
| Water | 15-25 |
| Aloe Water | 15-25 |
| Apple Pectin | 0.1-15 |
| Lecithin | 0.1-15 |
| Sorbitol | 0.1-15 |
| Inulin | 0.1-15 |
| Glycerin | 0.1-15 |
| Manuka honey | 0-10 |
| Malic acid | 0.1-10 |
| Chitosan | 0.1-10 |
| Ascorbic acid | 0.1-1.0 |
| Slippery Elm | 0.1-1.0 |
| Citric acid | 0.1-1.0 |
| Potassium sorbate | 0.01-5 |
| Apple powder/flavoring | 5-30 |
| Beet root powder | 0.1-10 |
| Hyaluronic acid | 0.1-25 |
| Schizophyllan | 0.1-10 |
| Propylparaben/methylparaben | 0.01-2 |
| Milk thistle | 0.1-10 |
| Dandelion root | 0.1-10 |
| Reishi mushroom | 0.1-10 |
| N-acetyl L-cysteine | 0.1-10 |
| Artichoke | 0.1-10 |

The compositions of the invention are administered, for example, on a daily basis. The amount administered can range from about 1 to about 10 mg/kg/day once, twice or more daily; or from about 1 to about 5 mg/kg/day, from about 1 to about 8 mg/kg/day, from about 1 to about 10 mg/kg/day, or from about 2 to about 4 mg/kg/day once, twice or more daily. In other embodiments, a composition of the invention is administered, for example, twice daily, three times daily, four times daily, or more than four times daily. The amount of the composition administered will vary with the weight of the animals. A foal, which weighs about 50 kg would receive about 1, 3, 5 or 10 g of a composition of the invention per day, i.e., about 1 g/50 kg, 3 g/50 kg, 1 g/10 kg, or 1 g/5 kg per day. In contrast, a full grown horse weighing 500 kg, might receive up to 80 kg per day (i.e., 1 g/25 kg, 2 g/25 kg, 3 g/25 kg, 4 g/25 kg, 1 g/5 kg, 10 g/25 kg, 20 g/25 kg.)

Doses administered once or multiple times per day can be given for consecutive days, e.g., two days, three days, four days, five days, six, days, seven days, or more, in some embodiments. A dose administered multiple times per day may embrace two, three, four, five, six, ten, or more times per day. Other dosing schedules, such as every other day, or every third day, every fourth day, etc. are embraced by the invention. In addition, one having skill in the art will appreciate that doses and amounts administered to the animal can vary, given the wide range of weights of the animals undergoing treatment, as well as the animal species and type of digestive system, e.g., ruminant or non-ruminant.

Methods of Use

The invention is directed to methods of treating and preventing hepatic insufficiency in young and adult animals, particularly equine animals, such as horses that can be naturally high-strung and can become stressed as a result of events in their habitats and lifestyles, as well as from endurance activities and performances expected of them. The method of the invention comprises administering to an animal in need of liver disease treatment or prevention. Treating the liver can also involve decreasing the discomfort and pain associated with hepatic insufficiency or injury in the animal undergoing treatment.

The non-human young and adult animals for which the treatment methods are suitable may include different animal types, genera, or species. In general, young and adult farm animals, animals bred or kept for various purposes, such as sport (e.g., racing, riding, dressage), transport, domestic, companion (e.g., dogs, cats), industrial uses (e.g. hauling, pulling, plowing), and the like, are particularly amenable to treatment according to the methods of the invention. For example, encompassed by the methods of the invention is the treatment of adult or young non-human animals, such as camels (calves), sheep (lambs), rams, horses (foals), pigs (piglets), goats (kids), bison/buffalo (calves), llamas, donkeys, mules, yaks, etc. Neonatal, young and adult exotic animals, such as zoo animals of various species, are also embraced by the treatments of the invention. In preferred aspects, young and adult horses are animal subjects that are particularly amenable to the methods and compositions of the invention. The compositions, formulations and methods as described herein are further suitable for use in humans.

EXAMPLE 1

Formula 1

A paste for oral delivery to an equine was produced. The paste contained the following materials:
Apple powder/flavoring . . . 16%
Water/aloe water . . . 45.2% (50/50 split)
Lecithin . . . 2.8%
Apple pectin . . . 4.8%
Sorbitol . . . 4.8%
Glycerin . . . 1.8%
Beet root powder . . . 4.1%
Inulin . . . 1.9%
Malic acid . . . 1.6%
Chitosan . . . 0.7%
Artichoke extract . . . 2.7%
Ascorbic acid . . . 0.4%
Citric acid . . . 0.5%
Potassium sorbate . . . 0.2%
Propylparaben . . . 0.1%
Milk thistle . . . 1.5%
Dandelion root . . . 4.1%
N-acetyl L-cysteine . . . 2.7%
Reishi mushroom . . . 4.1%

Under a veterinarian's supervision, the formulation was administered to horses in training. Liver enzyme levels were measured (Table 2).

TABLE 2

| Liver Enzyme Levels (gamma-glutamyl transferase; GGT) | | | |
|---|---|---|---|
| Test Subject (equine) | GGT (initial) (U/L) | GGT (day 14) (U/L) | % change |
| Hank | 17 | 17 | 0.00% |
| Bucket | 18 | 15 | 16.67% |
| Miss Fatty | 25 | 20 | 20.00% |
| Chachi | 16 | 14 | 12.50% |
| Money | 16 | 15 | 6.25% |

An improvement in the horses' physical performance was observed, indicating that the administration had been effective in decreasing gamma-glutamyl transferase (GGT) levels verified using blood tests. The horses showed an average drop of 11.08% in GGT in two weeks.

EXAMPLE 2

Formulation 2

A composition for delivery to an equine was produced. The composition contained the following materials:
Apple powder/flavoring . . . 15%
Water/aloe water . . . 46.2% (50/50 split)
Lecithin . . . 2.8%
Apple pectin . . . 3.8%
Sorbitol . . . 5.8%
Glycerin . . . 1.8%
Beet root powder . . . 4.1%
Inulin . . . 1.9%
Malic acid . . . 1.6%
Chitosan . . . 1.9%
Artichoke extract . . . 2.5%
Ascorbic acid . . . 0.4%
Citric acid . . . 0.5%
Potassium sorbate . . . 0.2%
Propylparaben . . . 0.1%
Milk thistle . . . 1.5%
Dandelion root . . . 3.6%
N-acetyl L-cysteine . . . 2.7%
Reishi mushroom . . . 3.6%

Under a veterinarian's supervision, the formulation was administered to horses suffering from ulcers. In embodiments, the formulation may be administered to other mammalian subjects, including humans.

EXAMPLE 3

Formulation 3

A composition of Formula 3 was produced for delivery to a subject, particularly a subject with an inflammatory disease or condition, such as liver inflammation. The composition was delivered to an equine animal to reduce liver inflammation. The composition may be administered to a mammal, such as a human or other mammalian subject. The composition contained the following materials:

Apple powder/flavoring . . . 14.8%
Flax seed . . . 17.25%
Omega 3 fish oil liquid . . . 38.9%
Apple fiber . . . 5.8%
Sorbitol . . . 4.9%
Beet root powder . . . 2.5%
Inulin . . . 0.8%
Malic acid . . . 1.6%
Chitosan . . . 0.37%
Ascorbic acid . . . 0.25%
Citric acid . . . 0.44%
Potassium sorbate . . . 0.1%
Milk thistle . . . 2.5%
Dandelion root . . . 2.5%
N-acetyl L-cysteine . . . 2.5%
Acetyl-L-carnitine . . . 1.6%
5-adenosylmethionine . . . 0.8%
L-methionine . . . 1.6%
Glutathione . . . 0.8%

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A composition formulated for oral administration to a subject, the composition comprising an effective amount for treatment of a liver disease or a gastric ulcer of milk thistle, dandelion root, one or more antioxidant amino acids or precursors thereof, a plant-based pomace, and lecithin, wherein the composition comprises an emulsion, and wherein the composition comprises from about 0.1% (wt/wt) to about 15% (wt/wt) lecithin, from about 0.1% (wt/wt) to about 10% (wt/wt) milk thistle, from about 0.1% (wt/wt) to about 10% (wt/wt) dandelion root, and from about 0.1% (wt/wt) to about 10% (wt/wt) of the antioxidant amino acids or precursors thereof.

2. The composition of claim 1, wherein the antioxidant amino acid is n-acetyl L-cysteine.

3. The composition of claim 1, further comprising a biopolymer selected from the group consisting of chitosan, cellulose, collagen, and alginate.

4. The composition of claim 1, comprising beet root, reishi mushroom, artichoke, and n-acetyl L-cysteine.

5. The composition of claim 1, further comprising inulin or another prebiotic.

6. The composition of claim 1, further comprising one or more of aloe water and aloe vera.

7. The composition of claim 1, further comprising one or more acids selected from the group consisting of ascorbic acid, citric acid, malic acid, acetic acid, vinegar, apple cider vinegar, and rice vinegar.

8. The composition of claim 1, further comprising a plant-based composition derived from a fruit, vegetable, grain, or herb and selected from the group consisting of a powder, liquid, concentrate, and a lyophilized component.

9. The composition of claim 8, wherein the plant-based composition has anti-inflammatory activity.

10. The composition of claim 1, further comprising a preservative that is one or more of ascorbic acid, potassium sorbate, and citric acid and/or a polyol selected from the group consisting of glycerol, glycerine, glycerin, maltitol, sorbitol, xylitol, erythritol, and isomalt.

11. The composition of claim 1, wherein water makes up the balance of the solution, and represents no less than 60 wt % of the entire solution.

12. The composition of claim 1, further comprising a soluble or insoluble nano-particulate.

13. The composition of claim 1, further comprising one or more soluble or insoluble antimicrobial, antifungal, or antibacterial agents.

14. The composition of claim 1, further comprising an omega-3 fatty acid and/or hyaluronic acid.

15. The method of claim 1, further comprising 5-30% by weight of a flavoring, wherein the flavoring is selected from the group consisting of apple, apple butter, apple pectin, peppermint, and citrus.

16. The composition of claim 1, wherein the amount of milk thistle in the composition is less than or equal to the amount of dandelion root in the composition.

17. The composition of claim 1, wherein the composition is in the form of a chew, gel, liquid, or paste.

* * * * *